United States Patent [19]

Lesieur et al.

[11] Patent Number: 5,182,278
[45] Date of Patent: Jan. 26, 1993

[54] ANALGESIC BENZOXAZOLINONES HAVING AT THE 6-POSITION A 1-HYDROXY-3-MORPHOLINOPROPYL SIDE CHAIN

[75] Inventors: Daniel Lesieur, Gondecourt; Charles Lespagnol, Lambersart; Jacqueline Bonnet, Paris, all of France

[73] Assignee: Adir et Compagnie, Neuilly-sur-Seine, France

[21] Appl. No.: 737,322

[22] Filed: Jul. 29, 1991

Related U.S. Application Data

[62] Division of Ser. No. 485,057, Feb. 26, 1990, Pat. No. 5,132,305.

[30] Foreign Application Priority Data

Feb. 28, 1989 [FR] France ............... 89 02554

[51] Int. Cl.$^5$ ........................... C07D 413/06
[52] U.S. Cl. ..................... 514/233.8; 544/137; 548/221
[58] Field of Search ............... 514/375, 233.8; 548/221; 544/137

[56] References Cited

U.S. PATENT DOCUMENTS

| | | | |
|---|---|---|---|
| 4,558,060 | 12/1985 | Caignard | 548/221 |
| 4,960,778 | 10/1990 | Lesieur et al. | 544/368 |
| 5,034,401 | 7/1991 | Frost et al. | 514/312 |

FOREIGN PATENT DOCUMENTS

| | | | |
|---|---|---|---|
| 0390673 | 10/1990 | European Pat. Off. | 548/221 |
| 2491471 | 4/1982 | France | 514/375 |
| 82-11186 | 4/1982 | PCT Int'l Appl. | 514/375 |

OTHER PUBLICATIONS

European Journal of Medicinal Chemistry-Chimica Therapeutica for Jan.-Feb., 1976, vol. 11, No. 1, pp. 33–42.

*Primary Examiner*—Donald G. Daus
*Attorney, Agent, or Firm*—Gordon W. Hueschen

[57] ABSTRACT

Compounds of general formula (I):

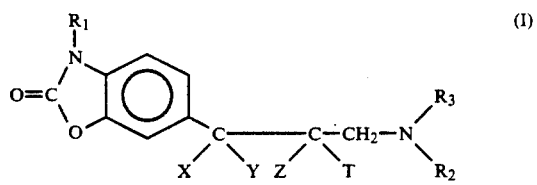

in which:
$R_1$ denotes a hydrogen atom or a lower alkyl optionally substituted with a hydroxyl group, $R_2$ and $R_3$:
a- identical or different, denote a hydrogen atom, a lower alkyl, a lower alkenyl, a substituted or unsubstituted aryl, a substituted or unsubstituted (lower alkyl-)aryl, b- are such that they form, with the nitrogen which carries them, a saturated or unsaturated, mono- or bicyclic heterocyclic system containing at most 3 hetero atoms per ring, substituted or unsubstituted, with the exception of 1-arylpiperazine systems, X denotes a hydrogen atom, Y denotes a hydrogen atom or a hydroxyl, or alternatively X and Y denote an oxygen atom, provided that $R_1$ is then other than a methyl group, Z denotes a hydrogen atom or forms a $\pi$ bond with Y, and T denotes a hydrogen atom or a lower alkyl, their stereoisomers and their quaternary ammonium salts, as well as their addition salts with a pharmaceutically acceptable acid having analgesic or arterial antihypertensive property.

Medicinal products.

6 Claims, No Drawings

ANALGESIC BENZOXAZOLINONES HAVING AT THE 6-POSITION A 1-HYDROXY-3-MORPHOLINOPROPYL SIDE CHAIN

The present application is a division of our prior-filed copending U.S. application Ser. No. 07/485,057, filed Feb. 26, 1990, now U.S. Pat. No. 5,132,305.

The present invention relates to new benzoxazolinone compounds, to their preparation and to pharmaceutical compositions containing them.

Many benzoxazolinone derivatives have been described in therapeutics as possessing a wide variety of pharmacological activities. French Patent 73/23,280 describes 6-acylbenzoxazolinones as analgesics French Patent 80/20,861 describes, in particular, 6-(2-aminoethyl)benzoxazolinones and 6-(aminoacetyl)benzoxazolinones which are usable in the treatment of arterial hypertension as well as in that of painful syndromes. French Patent 82/19,812 describes 6-(2-aminoethyl)-benzoxazolinones which are usable in therapy in the treatment of sleep disorders and character and behavioral disorders.

The Applicant has now discovered benzoxazolinone derivatives endowed with an analgesic activity which is devoid of anti-inflammatory activity, of a markedly more advantageous level than that of the derivatives described in French Patents 73/23,280 and 80/20,861. The compounds of the present invention are, in effect, endowed with a high-level pure analgesic activity. In point of fact, most non-morphinic analgesic substances known to date also possess anti-inflammatory activity (for example salicyl derivatives, pyrazole derivatives, etc.), and they consequently intervene in the processes occurring in inflammation. These processes involve a very large number of chemical mediators (prostaglandins, thromboxane A2, etc.); multifarious side effects accordingly ensue, the best known of which are attack of the gastric mucosa with the possibility of ulcers. Apart from the disturbances they cause, these concomitant effects prohibit the use of these products in many subjects who are especially sensitive to them. Being devoid of all anti-inflammatory activity, the compounds of the present invention do not interact with the mediators of inflammation and are hence devoid of the side effects mentioned above. This feature, combined, in the case of a number of the compounds, with a complete absence of toxicity and a high level of activity, renders some compounds of the present invention usable as analgesics much more safely and without the restrictions in use customarily known for the great majority of these products. Some compounds of the invention exhibit, in addition, advantageous activity on arterial blood pressure and on the central nervous system.

More specifically, the invention relates to the compounds of general formula (I):

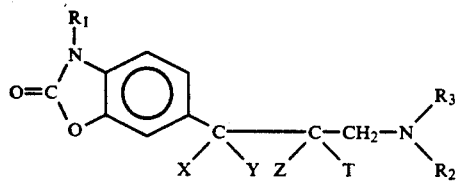

(I)

in which:

$R_1$ denotes a hydrogen atom or a lower alkyl group optionally substituted with a hydroxyl group, $R_2$ and $R_3$, which may be identical or different, denote
a hydrogen atom,
a linear or branched lower alkyl group,
a linear or branched lower alkenyl group,
an aryl or (lower alkyl)aryl group in which the aryl portion is optionally substituted with one or more halogen atoms, or lower alkyl groups optionally substituted with one or more halogen atoms, or lower alkoxy groups, or alternatively $R_2$ and $R_3$ form, with the nitrogen atom to which they are attached, a saturated or unsaturated, mono- or bicyclic heterocyclic system containing one, two or three hetero atoms per ring, chosen from nitrogen, oxygen or sulfur, unsubstituted or substituted with a halogen or a lower alkyl, lower alkoxy or aryl group optionally substituted with one or more halogen atoms, provided that $R_2$ and $R_3$ do not form a 1-arylpiperazine system with the nitrogen atom to which they are attached, X denotes a hydrogen atom,
denotes a hydrogen atom or a hydroxyl group, or alternatively X and Y together denote an oxygen atom provided that, in this case, R is other than a methyl group, Z denotes a hydrogen atom or alternatively Z forms a $\pi$ bond with Y, and T denotes a hydrogen atom or a lower alkyl group,
the term lower indicating that the groups so described have from 1 to 6 carbon atoms,
their enantiomers, diastereoisomers and epimers and their quaternary ammonium salts as well as their addition salts with a pharmaceutically acceptable acid.

Among acids which may be used for salifying compounds of general formula (I), hydrochloric, sulfuric, phosphoric, tartaric, malic, maleic, fumaric, oxalic, methanesulfonic, ethanesulfonic, camphoric and citric acids, and the like, may be mentioned without implied limitation.

The invention also encompasses two processes for the production of the compounds of formula (I).

Depending on the compounds of the invention which it is desired to obtain, it may, in effect, be advantageous to use either one process or the other.

The first process for preparing the compounds of formula (I), which is especially advantageous for the production of the compounds of formula (I) in which X, Y and Z each denote a hydrogen atom, can nevertheless be applied for the derivatives in which X, Y and Z have other meanings, and employs as starting material a derivative of formula (II):

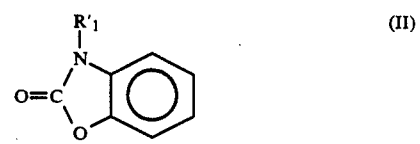

(II)

in which $R'_1$ denotes a hydrogen atom or a lower alkyl group,
the compound being obtained, for example, by the reaction of ortho-aminophenol with urea followed, when $R'_1$ is other than H, by an alkylation on the nitrogen, which compounds is subjected to the action of an acid chloride of formula (III):

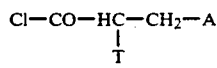

in which T has the same meaning as in the formula (I), A denoting a halogen atom,
or alternatively of the corresponding acid anhydride, in the presence of aluminum chloride in dimethylformamide according to the conditions of THYES et al. (J. Med. Chem. 1983, 26, 6, 800-807), to obtain a compound of formula (IV):

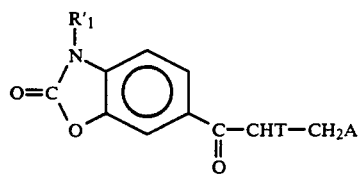

in which $R'_1$, T and A have the same meaning as above, which, if so desired, is subjected to reduction with a trialkylsilane in an acid medium according to the conditions described by WEST et al. (J. Org. Chem. 1973, 38, (15), 2675-2681), to lead to a compound of formula (V):

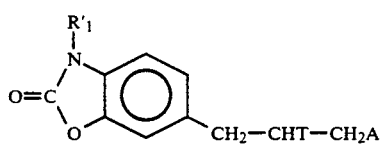

in which $R'_1$, T and A have the same meaning as above, the compound of formula (IV) or the compound of formula (V), depending on the formula of the compound of formula (I) which it is desired to obtain, then being subjected to the action of an amine of formula (VI):

in which $R_2$ and $R_3$ have the same meaning as in the formula (I),
in a solvent preferably chosen from acetone, acetonitrile, ethyl acetate, lower aliphatic alcohol, dioxane, benzene and toluene, at a temperature between room temperature and the boiling point of the chosen solvent, in the presence of an excess of the chosen amine or of a trapping agent for the hydracid formed, such as triethylamine,
to lead to a compound of formula (I/A):

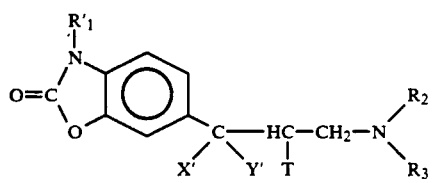

in which, depending on whether the starting material used is a compound of the formula (IV) or (V), X' and Y' together denote an oxygen atom, or alternatively X' and Y' each simultaneously denote a hydrogen atom,
$R'_1$, $R_2$, $R_3$ and T having the same meaning as above, which, if so desired, is salified with a pharmaceutically acceptable acid or which can, when X' and Y' together denote an oxygen atom, if so desired, be subjected either to a hydrogenating agent chosen from an alkali metal mixed hydride such as, for example, sodium borohydride, or an alkali metal mixed cyanohydride such as sodium cyanoborohydride, preferably in a lower aliphatic alcohol medium, to lead to a compound, of formula (I/B)—predominantly in the threo configuration when T does not denote a hydrogen atom:

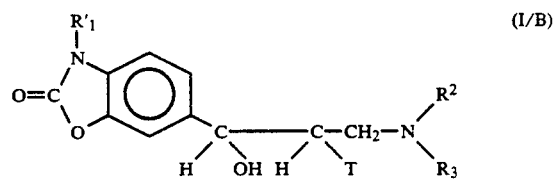

a special case of the compounds of formula (I) in which:
$R'_1$, $R_2$, $R_3$ T have the same meaning as above,
X denotes a hydrogen atom,
Y a hydroxyl group and Z a hydrogen atom,
the isomers of which are separated if so desired, and/or which is salified with a pharmaceutically acceptable acid,
or alternatively to catalytic hydrogenation, with heating and under pressure in a solvent chosen from lower aliphatic alcohol or dioxane, to lead to a compound of formula (I/B)—essentially in the erythro configuration when T does not denote a hydrogen atom the isomers of which are separated if so desired, and which is salified, where appropriate, with a pharmaceutically acceptable acid,
which compound of formula (I/B), irrespective of the process according to which it has been obtained, can, if so desired, be treated with a dehydrating agent, preferably chosen from hydracids, to lead to a compound formula (I/C):

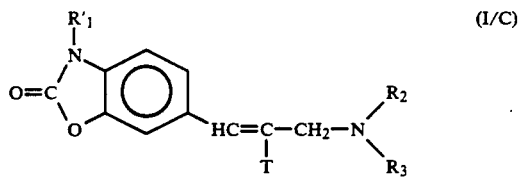

predominantly in the form of the trans isomer, a special case of derivatives of formula (I) in which:
$R'_1$, $R_2$, $R_3$ and T have the same meaning as above,
X denotes a hydrogen atom,
Z forms a $\pi$ bond with Y,
the cis/trans isomers of which are separated, if so desired, by a familiar technique such as chromatography on a silica column or crystallization, and which, if so desired, may be salified with a pharmaceutically acceptable acid,
which compound of formula (I/A), (I/B) or (I/C), when $R'_1$ denotes a hydrogen atom, may be treated in the presence of a strong base with a compound of formula $X—(CH_2)_n—OH$, in which X denotes a halogen atom and n is between 1 and 6, to lead to a compound of formula (I) for which R₁ denotes a lower alkyl group substituted with a hydroxyl group, which compound of formula (I) may be treated, if so desired, with a conventional alkylating agent such as methyl sulfate to lead to a quaternary ammonium salt.

The second process for the production of the compounds of the present invention is inapplicable for the compounds for which R₁ denotes a hydrogen atom or an alkyl group substituted with a hydroxyl group.

In this second process, a compound of formula (II), obtained as stated above:

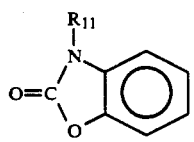
(II)

in which R₁₁ denotes a lower alkyl group, is acylated with an acid of formula (VII):

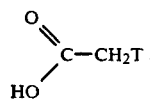
(VII)

in which T has the same meaning as in the formula (I), or the corresponding chloride or anhydride of the acid, according to the conditions described in French Patent 73/23,280,
to obtain a compound of formula (VIII):

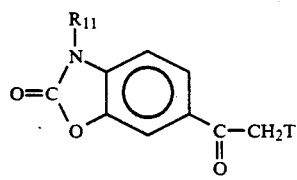
(VIII)

in which R₁₁ denotes a lower alkyl group and T has the same meaning as in the formula (I),
which is then treated
either according to the conditions of the Mannich reaction, which are well known to those versed in the art, in the presence of trioxymethylene and of the amine of formula (VI):

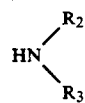
(VI)

in which R₂ and R₃ have the same meaning as in the formula (I),
to obtain a compound of formula (I/A1):

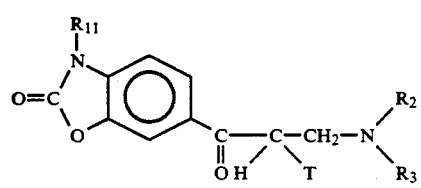
(I/A1)

a special case of the compounds of formulae (I/A) and (I) in which formula:
R₁₁ denotes a lower alkyl group, and R₂, R₃ and T have the same meaning as in the formula (I),
X and Y here simultaneously denote an oxygen atom and Z a hydrogen atom,
or alternatively with bis(dimethylamino)methane in the presence of acetic anhydride to obtain a product of general formula (IX):

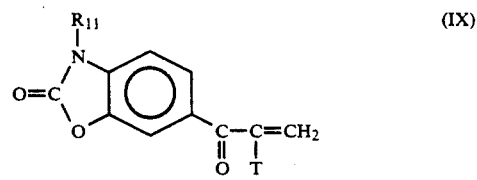
(IX)

in which:
T has the same meaning as in the formula (I) and R₁₁ denotes a lower alkyl group,
which is treated with an amine of formula (VI), in a polar solvent at a temperature between room temperature and the boiling point of the reaction medium, to lead to a compound of formula (I/AI) defined above, which, when T does not denote a hydrogen atom, can, if so desired, be separated into its isomers, which are salified, if so desired, with a pharmaceutically acceptable acid, and which can if so desired, be subjected:
either, preferably in a lower aliphatic alcohol medium, to a hydrogenating agent, preferably an alkali metal mixed hydride or an alkali metal mixed cyanohydride such as, for example, sodium borohydride or sodium cyanoborohydride,
to lead to a compound . of formula (I/B), predominantly in the threo configuration (when T does not denote a hydrogen atom):

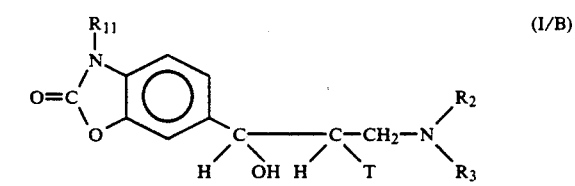
(I/B)

a special case of the compounds of formula (I) in which:
R₁₁, R₂, R₃ and T have the same meaning as above,
X denotes a hydrogen atom,
Y a hydroxyl group and Z a hydrogen atom,
the isomers of which are separated if so desired, and which may be salified with a pharmaceutically acceptable acid,
or alternatively to catalytic hydrogenation, in a solvent chosen from lower aliphatic alcohol or dioxane, to lead to a compound of formula (I/B), essentially in the erythro configuration—when T does not denote a hydrogen atom—the isomers of which are separated if so desired, and which is salified, where appropriate, with a pharmaceutically acceptable acid,
which compound of formula (I/B) is, where appropriate, subjected to a dehydrating agent preferably chosen from hydracids, to lead to a compound of formula (I/C), predominantly in the form of trans isomers:

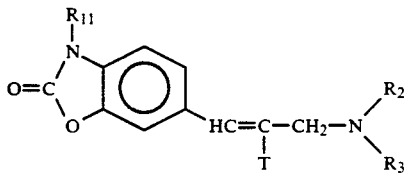

a special case of compounds of formula (I) in which:
$R_{11}$, $R_2$, $R_3$ and T have the same meaning as in the compounds of formula (I),
X denotes a hydrogen atom,
Z forms a π bond with Y,
the cis/trans isomers of which are separated, if so desired, by a familiar technique such as chromatography on a silica column or crystallization,
and which is salified, if so desired, with a pharmaceutically acceptable acid,
which, if so desired, is subjected to a catalytic hydrogenation reaction, preferably at room temperature and atmospheric pressure and in the presence of Raney nickel in a lower aliphatic alcohol or dioxane medium, to obtain a compound of formula (I/D):

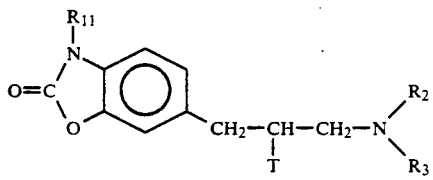

in which:
$R_{11}$, $R_2$, $R_3$ and T have the same meaning as above,
X, Y and Z each simultaneously denotes a hydrogen atom,
the isomers of which are separated, where appropriate, when T does not denote a hydrogen atom,
and which is optionally salified with a pharmaceutically acceptable acid or which is converted to a quaternary ammonium salt by the action of an alkylating agent as stated above.

The compounds of formula (I/D) may also be obtained from the derivatives of formula (IX):

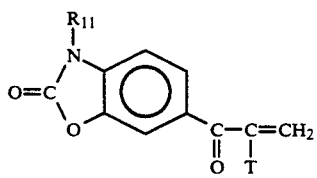

in which:
$R_{11}$ and T have the same meaning as above, which are treated with a hydracid to obtain a derivative of formula (IV):

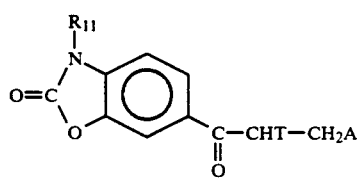

in which $R_{11}$ and T have the same meaning as above and A the same meaning as in the formula (III),
the isomers of which are separated, if so desired, when T does not denote a hydrogen atom,
which is subjected to reduction with a trialkylsilane in an acid medium according to the conditions described by WEST et al. (J. Org. Chem 1973, 38, (15), 2675-2681), to lead to a compound of formula (V):

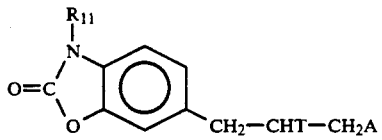

in which $R_{11}$ and T have the same meaning as above and A the same meaning as in the formula (III),
which is subjected to the action of an amine of formula (VI):

in which $R_2$ and $R_3$ have the same meaning as in the formula (I), in a solvent preferably chosen from acetone, acetonitrile, ethyl acetate, lower aliphatic alcohol, dioxane, benzene and toluene, at a temperature between room temperature and the boiling point of the chosen solvent, in the presence of an excess of the chosen amine or of a trapping agent for the hydracid formed, such as triethylamine,
to lead to a compound of formula (I/D) designated above, which is salified, if so desired, with a pharmaceutically acceptable acid or which is converted to a quaternary ammonium salt with an alkylating agent.

The compounds of formula (I) possess advantageous pharmacological properties.

In particular, these compounds have evinced an advantageous analgesic activity as well as, in the case of some of these compounds, an activity on the central nervous system and on arterial blood pressure.

A pharmacological study of the compounds of the invention showed, in effect, that they were of low toxicity, endowed with a pure analgesic activity and hence devoid of drawbacks inherent in most non-morphinic compounds exhibiting this activity (ulcerogenic action on the mucosae, etc.). This spectrum of activity hence renders the compounds of the present invention advantageous in a number of indications such as rheumatic pain, lumbosciatic neuralgia, cervicobrachial neuralgia, pain associated with trauma such as sprains, fractures, dislocations, post-traumatic pain, postoperative pain, dental pain, neurological pain such as facial neuralgia, visceral pain such as nephritic colic, pain associated with dysmenorrhea and proctological surgery, pain of the ENT region, pancreatitis, various pains, headache, cancer pain, etc.

The subject of the present invention is also pharmaceutical compositions containing the products of formula (I), alone or in combination with one or more pharmaceutically acceptable, non-toxic, inert vehicles or excipients.

Among pharmaceutical compositions according to the invention, there may be mentioned, more especially, those which are suitable for oral, parenteral and nasal administration, simple or sugar-coated tablets, sublingual tablets, sachets, packets, gelatin capsules, sublingual preparations, pills, suppositories, creams, ointments, skin gels, and the like.

The appropriate dosage varies according to the patient's age and weight, the administration route, the nature of the therapeutic indication and any associated treatments, and ranges between 1 centigram and 4 grams per 24 hours.

The examples which follow illustrate the invention and in no way limit the latter.

The infrared spectra were run using a potassium bromide disk containing approximately 1% of the test product.

EXAMPLE 1:
3-METHYL-6-[3-(1-PIPERIDYL)PROPYL]BENZOXAZOLINONE (HYDROCHLORIDE)

Stage A:
3-methyl-6-(3-chloropropionyl)benzoxazolinone 6.02 ml (0.078 mole) of dimethylformamide are introduced dropwise and with stirring into a ground-necked flask containing 37.4 g (0.28 mole) of anhydrous aluminum chloride.

The flask is equipped with a reflux condenser and taken to an oil bath at a temperature in the region of 40°–45° C. 0.04 mole of 3-methylbenzoxazolinone and 0.44 mole of 3-chloropropionic acid chloride are introduced. The mixture is heated to a temperature in the region of 75° C. for 2 hours 30 minutes. After cooling, the reaction mixture is poured into 300 g of ice, acidified with concentrated hydrochloric acid and stirred for hour 30 minutes. The precipitate obtained is drained, washed with water and dried. The product is recrystallized in ethanol.

Yield: 88%.
Melting point: 187° C.
Infrared: $\nu$ CO (carbamate): 1765 cm$^{-1}$; $\nu$ CO (ketone): 1660 cm$^{-1}$;

Stage B: 3-methyl-6-(3-chloropropyl)benzoxazolinone 0.02 mole of 3-methyl-6-(3-chloropropionyl)benzoxazolinone, obtained in the preceding stage, is dissolved in 22.8 g (0.2 mole) of trifluoroacetic acid in a ground-necked flask 0.044 mole of triethylsilane is added dropwise and while cooling. A calcium chloride guard tube is fitted and stirring is continued for 72 hours. The reaction medium is then poured into ice-cold water and the precipitate obtained is drained, dried and recrystallized in hexane.

Yield: 80%.
Melting point 70° C.
Infrared: $\nu$ CO (carbamate): 1775 cm$^{-1}$;

Stage C:
3-methyl-6-[3-(1-piperidyl)propyl]benzoxazolinone (Hydrochloride)

0.02 mole of 3-methyl-6-(3-chloropropyl)benzoxazolinone, obtained in stage B, is dissolved in acetonitrile in a 250-cm$^3$ ground-necked flask equipped with a condenser 0.04 mole of piperidine is added with magnetic stirring and the mixture is brought to reflux for 48 hours. After cooling of the solution, the insoluble matter formed is filtered off and the filtrate is then evaporated on a water bath under vacuum. The residue is taken up with 500 cm$^3$ of water and the mixture is alkalinized with 10% strength aqueous sodium hydroxide solution. The precipitate is drained and washed with water until the aqueous phase is neutral, and the compound is then dissolved in hexane and a stream of gaseous hydrochloric acid is bubbled through. The product is drained, dried and recrystallized in ethanol.

Yield: 69%.
Melting point: 238° C.
Infrared: $\nu$ CO: 1770 cm$^{-1}$.

EXAMPLE 2:
3-METHYL-6-[3-(4-METHYL-1-PIPERAZINYL)-PROPYL]BENZOXAZOLINONE (DIHYDROCHLORIDE)

0.02 mole of 3-methyl-6-(3-chloropropyl)benzoxazolinone, obtained in stage B of Example 1, is dissolved in dioxane in a 250-cm$^3$ ground-necked flask equipped with a condenser 0.04 mole of N-methylpiperazine is added with stirring and the mixture is brought to reflux for 48 hours After cooling of the solution, the insoluble matter is filtered off and the filtrate is then evaporated on a water bath under vacuum. The residue is taken up with 500 cm$^3$ of water and the mixture is alkalinized with 10% strength aqueous sodium bicarbonate solution and extracted with chloroform. The organic phase is dried over calcium chloride, filtered and evaporated to dryness. An oily product is obtained, which is taken up with acetone. After gaseous hydrochloric acid has been bubbled through this solution, the product is drained, dried and recrystallized in a methanol/acetone mixture.

Yield: 53%.
Melting point: >270° C.
Infrared: $\nu$ CO: 1770 cm$^{-1}$.

EXAMPLE 3:
3-METHYL-6-[3-(1-PYRROLIDINYL)PROPYL]-BENZOXAZOLINONE (HYDROCHLORIDE)

0.02 mole of 3-methyl-6-(3-chloropropyl)benzoxazolinone, obtained in stage B of Example 1, is dissolved in acetonitrile in a 250-cm$^3$ ground-necked flask equipped with a condenser. 0.04 mole of pyrrolidine, 0.02 mole of potassium iodide and 0.02 mole of sodium carbonate are added with stirring and the mixture is brought to reflux for 4 days. After cooling of the solution, the insoluble matter is filtered off and the filtrate is then evaporated on a water bath under vacuum. The residue is taken up in ether, the remaining insoluble matter is filtered off and a stream of gaseous hydrochloric acid is bubbled through this solution. The product is drained, dried and recrystallized in acetone.

Yield: 69%.
Melting point: 174° C.
Infrared $\nu$ CO: 1770 cm$^{-1}$.

EXAMPLE 4:
3-METHYL-6-(1-HYDROXY-3-MORPHOLINO-PROPYL)BENZOXAZOLINONE

Stage A:
3-methyl-6-(3-morpholinopropionyl)benzoxazolinone 0.03 mole of 6-acetyl-3-methylbenzoxazolinone, obtained as described in French Patent 73/23,280, and 0.045 mole of morpholine hydrochloride are dissolved in 150 cm$^3$ of absolute ethanol in a 250-cm$^3$ ground-necked flask equipped with a condenser 0.045 mole of trioxymethylene is added and the mixture is acidified with hydrochloric acid. The mixture is heated to reflux for 64 hours. The precipitate formed is drained, washed with acetone and suspended in water and the mixture is alkalinized with sodium hydroxide. The mixture is extracted several times with chloroform, the organic phases are dried over sodium chloride, filtered and evaporated on a water bath under vacuum and the product is recrystallized in ethanol.

Yield: 55%.
Melting point: 134° C.
Infrared $\nu$ CO (carbamate): 1770 cm$^{-1}$; $\nu$CO (ketone): 1660 cm$^{-1}$.

STAGE B: 3-methyl-6-(1-hydroxy-3-morpholinopropyl)benzoxazolinone 0.01 mole of 3-methyl-6-(3-morpholinopropionyl)-benzoxazolinone, prepared in stage A, is dissolved in 200 cm$^3$ of methanol in a 250-cm$^3$ flask equipped with a magnetic stirrer 0.02 mole of sodium borohydride is added very slowly and with stirring. Stirring is continued for 4 hours at room temperature. The reaction medium is evaporated on a water bath under vacuum. The residue is taken up with water and the mixture is extracted several times with chloroform. The extracts are filtered and evaporated to dryness on a water bath under vacuum and the product is recrystallized in cyclohexane.

Yield: 68%.
Melting point: 115° C.
Infrared: $\nu$ CO: 1755 cm$^{-1}$.

EXAMPLE 5:
3-METHYL-6-(3-MORPHOLINO-1-PROPENYL)-BENZOXAZOLINONE 0.015 mole of 3-methyl-6-(1-hydroxy-3-morpholinopropyl)benzoxazolinone, obtained in Example 4, is dissolved in 50 cm$^3$ of 47% strength hydrobromic acid in a 250-cm$^3$ flask, and the solution is stirred at room temperature for 2 hours. The precipitate is drained, washed with acetone and suspended in water and the mixture is alkalinized with sodium hydroxide. The mixture is extracted several times with chloroform, the organic phases are combined and dried over calcium chloride, filtered and evaporated to dryness under vacuum and the product is recrystallized in propanol.

Yield: 64%.
Melting point: 132° C.
Infrared: $\nu$ CO: 1765 cm$^1$.

EXAMPLE 6:
3-METHYL-6-(3-MORPHOLINOPROPYL)BENZOXAZOLINONE 0.01 mole of 3-methyl-6-[(3-morpholino)-1-propenyl]-benzoxazolinone, obtained in Example 5, is dissolved in methanol in a 500-cm$^3$ conical flask equipped with a three-way tap and a magnetic stirrer, and 0.5 g of Raney nickel is then added. The mixture is stirred under a hydrogen atmosphere at room temperature and atmospheric pressure. After the theoretical amount of hydrogen has been absorbed, the reaction medium is filtered and the filtrate is evaporated to dryness on a water bath under vacuum. The residue is taken up with water, the mixture is acidified with hydrochloric acid and the precipitate is drained and recrystallized in ethyl acetate.

Yield: 86%.
Melting point: 226° C.
Infrared: $\nu$ CO: 1770 cm$^{-1}$.

EXAMPLE 7:
3-METHYL-6-(3-MORPHOLINOPROPYL)BENZOXAZOLINONE

Using the procedure described in Example 1, but replacing piperidine (stage C) by morpholine, the expected product is obtained.

EXAMPLE 8:
3-METHYL-6-(3-DIETHYLAMINOPROPYL)BENZOXAZOLINONE

Using the procedure described in Example 1, but replacing piperidine (stage C) by N,N-diethylamine, the expected product is obtained.

Melting point: 131°–132° C.

EXAMPLE 9:
6-(3-MORPHOLINOPROPYL)BENZOXAZOLINONE (HYDROCHLORIDE)

Stage A: 6-(3-chloropropionyl)benzoxazolinone 56.1 g (0.42 mole) of aluminum chloride are weighed into a ground-necked flask, 10 cm$^3$ of dimethylformamide are then added using a dropping funnel and the mixture is left stirring until it becomes homogeneous. 8.1 g (0.06 mole) of benzoxazolinone are then added and the mixture is left stirring for 10 minutes before adding (0.072 mole) of 3-chloropropionic acid chloride. This mixture is maintained in an oil bath at 80°–85° C. for approximately 2 hours 30 minutes. After cooling, the reaction mixture is poured into ice-cold water. The precipitate is drained and washed with water to neutrality. The product is recrystallized in ethanol.

Yield: 70%.
Melting point: 166° C.
Infrared: $\nu$ CO (carbamate): 1760 cm$^{-1}$; $\nu$ CO (ketone): 1655 cm$^{-1}$.

Stage B: 6-(3-chloropropyl)benzoxazolinone 9 g (0.04 mole) of 6-(3-chloropropionyl)benzoxazolinone, obtained in stage A, and 31 cm$^3$ of trifluoroacetic acid are introduced into a ground-necked flask 13.5 cm$^3$ (0.09 mole) of triethylsilane are added dropwise using a dropping funnel and with stirring. The dropping funnel is replaced by a calcium chloride guard tube and the mixture is left stirring at room temperature for 48 hours. The reaction mixture is then poured into ice-cold water and the mixture is left stirring for 2 hours. The precipitate is drained and washed with water to neutrality. The product is recrystallized in toluene.

Yield: 70%.
Melting point: 127° C.
Infrared: $\nu$ CO: 1770 cm$^{-1}$.

Stage C: 6-(3-morpholinopropyl)benzoxazolinone (Hydrochloride)

4.2 g (0.02 mole) of 6-(3-chloropropyl)benzoxazolinone are dissolved in 100 cm$^3$ of acetonitrile in a round-bottomed flask. 2.0 g (0.02 mole) of morpholine and 2.4 g (0.02 mole) of triethylamine are added and the mixture is left stirring under reflux for 5 days. After cooling, the reaction mixture is evaporated to dryness, the residue is taken up several times with anhydrous acetone and the triethylamine hydrochloride formed is filtered off. The acetone is evaporated off, the residue is taken up with an acetone/hexane mixture and a stream of gaseous hydrochloric acid is bubbled through this solution. The precipitate is drained and dried and then recrystallized in acetone.
Yield: 43%.
Melting point: 120° C.
Infrared: ν CO: 1750 cm$^{-1}$.

EXAMPLE 10:
6-[3-(1-PIPERIDYL)PROPYL]BENZOXAZOLINONE

Using the procedure described in Example 9, but replacing morpholine (stage C) by piperidine, the expected product is obtained.

EXAMPLE 11:
6-[3-(4-METHYL-1-PIPERAZINYL)PROPYL]BENZOXAZOLINONE

Using the procedure described in Example 9, but replacing morpholine (stage C) by 4-methylpiperazine, the expected product is obtained.

EXAMPLE 12:
6-[3-(1-PYRROLIDINYL)PROPYL]BENZOXAZOLINONE

Using the procedure described in Example 9, but replacing morpholine (stage C) by pyrrolidine, the expected product is obtained.

EXAMPLE 13:
6-(3-DIETHYLAMINOPROPYL)BENZOXAZOLINONE

Using the procedure described in Example 9, but replacing morpholine (stage C) by diethylamine, the expected product is obtained.

EXAMPLE 14:
3-METHYL-6-[3-(3-THIAZOLIDINYL)PROPYL]-BENZOXAZOLINONE

Using the procedure described in Example 1, but replacing piperidine (stage C) by thiazolidine, the expected product is obtained.

EXAMPLE 15
6-[3-(3-THIAZOLIDINYL)PROPYL]BENZOXAZOLINONE

Using the procedure described in Example 9, but replacing morpholine (stage C) by thiazolidine, the expected product is obtained.

EXAMPLE 16:
3-METHYL-6-(3-DIMETHYLAMINOPROPYL)-BENZOXAZOLINONE

Using the procedure described in Example 1, but replacing piperidine (stage C) by dimethylamine, the expected product is obtained.

EXAMPLE 17
6-(3-DIMETHYLAMINOPROPYL)BENZOXAZOLINONE

Using the procedure described in Example 9, but replacing morpholine (stage C) by dimethyl-amine, the expected product is obtained.

EXAMPLE 18:
3-METHYL-6-[3-(1-INDOLINYL)PROPYL]BENZOXAZOLINONE

Using the procedure described in Example 1, but replacing piperidine (stage C) by indoline, the expected product is obtained.

EXAMPLE 19:
6-[3-(1-INDOLINYL)PROPYL]BENZOXAZOLINONE

Using the procedure described in Example 9, but replacing morpholine (stage C) by indoline, the expected product is obtained.

EXAMPLE 20:
3-METHYL-6-[1-HYDROXY-3-(1-PIPERIDYL)-PROPYL]BENZOXAZOLINONE

Using the procedure described in Example 4, but replacing morpholine hydrochloride (stage A) by piperidine hydrochloride, the expected product is obtained.

EXAMPLE 21:
3-METHYL-6-(3-PIPERIDYL-1-PROPENYL)BENZOXAZOLINONE

Using the procedure described in Example 5, but replacing 3-methyl-6-(1-hydroxy-3-morpholinopropyl)-benzbenzoxazolinone by 3-methyl-6-(1-hydroxy-3-piperidylpropyl)benzoxazolinone (Example 20), the expected product is obtained.

EXAMPLE 22:
3-METHYL-6-[3-(1-PIPERIDYL)PROPYL]BENZOXAZOLINONE

Using the procedure described in Example 6, but replacing 3-methyl-6-(3-morpholino-1-propenyl)benzoxazolinone by 3-methyl-6-(3-piperidyl-1-propenyl)-benzoxazolinone (Example 21), the expected product is obtained.

EXAMPLE 23:
3-METHYL-6-[1-HYDROXY-3-(4-METHYL-1-PIPERAZINYL)PROPYL]BENZOXAZOLINONE

Using the procedure described in Example 4, but replacing morpholine hydrochloride (stage A) by 1-methylpiperazine dihydrochloride, the expected product is obtained.

EXAMPLE 24:
3-METHYL-6-[3-(4-METHYL-1-PIPERAZINYL)-1-PROPENYL]BENZOXAZOLINONE

Using the procedure described in Example 5, but replacing 3-methyl-6-(1-hydroxy-3-morpholinopropyl)-benzoxazolinone by 3-methyl-6-[1-hydroxy-3-(4-methyl-1piperazinyl)propyl]benzoxazolinone (Example 23), the expected product is obtained.

EXAMPLE 25:
3-METHYL-6-[3-(4-METHYL-1-PIPERAZINYL)-PROPYL]BENZOXAZOLINONE

Using the procedure described in Example 6, but replacing 3-methyl-6-(3-morpholino-1-propenyl)benzoxazolinone by 3-methyl-6-[3-(4-methyl-1-piperazinyl)-1propenyl]benzoxazolinone (Example 24), the expected product is obtained.

EXAMPLE 26:
3-METHYL-6-(1-HYDROXY-3-DIMETHYLAMINOPROPYL)BENZOXAZOLINONE

Using the procedure described in Example 4, but replacing morpholine hydrochloride (stage A) by dimethylamine hydrochloride, the expected product is obtained.

EXAMPLE 27:
3-METHYL-6-(3-DIMETHYLAMINO-1-PROPENYL)BENZOXAZOLINONE

Using the procedure described in Example 5, but replacing 3-methyl-6-(1-hydroxy-3-morpholinopropyl)-benzoxazolinone by 3-methyl-6-(1-hydroxy-3-dimethylaminopropyl)benzoxazolinone (Example 26), the expected product is obtained.

EXAMPLE 28:
3-METHYL-6-(3-DIMETHYLAMINOPROPYL)-BENZOXAZOLINONE

Using the procedure described in Example 6, but replacing 3-methyl-6-(3-morpholino-1-propenyl)benzoxazolinone by 3-methyl-6-(3-dimethylamino-1-propenyl)benzoxazolinone (Example 27), the expected product is obtained.

EXAMPLE 29:
3-METHYL-6-[1-HYDROXY-3-(1-PYRROLIDINYL)PROPYL]BENZOXAZOLINONE

Using the procedure described in Example 4, but replacing morpholine hydrochloride (stage A) by pyrrolidine dihydrochloride, the expected product is obtained.

EXAMPLE 30:
3-METHYL-6-[3-(1-PYRROLIDINYL)1-PROPENYL]BENZOXAZOLINONE

Using the procedure described in Example 5, but replacing 3-methyl-6-(1-hydroxy-3-morpholinopropyl)-benzoxazolinone by 3-methyl-6-[1-hydroxy-3-(1-pyrrolidinyl)propyl]benzoxazolinone (Example 29), the expected product is obtained.

EXAMPLE 31:
3-METHYL-6-[3-(1-PYRROLIDINYL)PROPYL]-BENZOXAZOLINONE

Using the procedure described in Example 6, but replacing 3-methyl-6-(3-morpholino-1-propenyl)benzoxazolinone by 3-methyl-6-[3-(1-pyrrolidinyl)-1-propenyl]benzoxazolinone (Example 30), the expected product is obtained.

EXAMPLE 32:
3-METHYL-6-[1-HYDROXY-3-(3-THIAZOLIDINYL)PROPYL]BENZOXAZOLINONE

Using the procedure described in Example 4, but replacing morpholine hydrochloride (stage A) by thiazolidine hydrochloride, the expected product is obtained.

EXAMPLE 33:
3-METHYL-6-[3-(3-THIAZOLIDINYL)-1-PROPENYL]BENZOXAZOLINONE

Using the procedure described in Example 5, but replacing 3-methyl-6-(1-hydroxy-3-morpholinopropyl)-benzoxazolinone by 3-methyl-6-[1-hydroxy-3-(3-thiazolidinyl)propyl]benzoxazolinone (Example 32), the expected product is obtained.

EXAMPLE 34:
3-METHYL-6-[3-(3-THIAZOLIDINYL)-1-PROPYL]BENZOXAZOLINONE

Using the procedure described in Example 6, but replacing 3-methyl-6-(3-morpholino-1-propenyl)benzoxazolinone by 3-methyl-6-[3-(3-thiazolidinyl)-1-propenyl]benzoxazolinone (Example 33), the expected product is obtained.

EXAMPLE 35:
6-(3-MORPHOLINOPROPYL)-3-(2-HYDROXYETHYL)BENZOXAZOLINONE (HYDROCHLORIDE)

0.01 mole of 6-(3-morpholinopropyl)benzoxazolinone hydrochloride, obtained in Example 9, is added to sodium ethylate. The reactants are left in contact for one hour, the mixture is evaporated to dryness, the residue is taken up with 20 cm$^3$ of DMF and 1.2 equivalents of 2-bromoethanol are added in the cold state with stirring. The mixture is stirred overnight at room temperature. The DMF is evaporated off to dryness, the residue is taken up with water and the aqueous phase is extracted with chloroform. The extracts are dried over CaCl$_2$, filtered and evaporated to dryness.

The residue is taken up with an acetone/ether mixture, the resulting mixture is filtered and a stream of gaseous hydrochloric acid is bubbled through; the product precipitates. It is recrystallized in propanol.

Yield: 50%.
Melting point: 209°–210° C.

EXAMPLE 36:
6-[3-(N-METHYLMORPHOLINO)PROPYL]-3-METHYLBENZOXAZOLINONE METHANESULFONATE 0.03 mole of 3-methyl-6-(3-chloropropyl)benzoxazolinone is dissolved in 100 cm$^3$ of acetonitrile 5.2 cm$^3$ of morpholine are added and the mixture is left stirring under reflux for 48 hours. The mixture is cooled and drained, the filtrate is evaporated, the residue is taken up with water and the mixture is alkalinized with 19% strength sodium hydroxide. The aqueous phase is extracted with chloroform and the extracts are dried over calcium chloride, filtered and evaporated to dryness.

The residue is taken up with anhydrous chloroform and 0.03 mole of methyl sulfate is added. The mixture is left stirring under reflux for one hour. The product precipitates; it is drained and recrystallized in ethanol.

Yield: 65%.
Melting point: 142° C.

Pharmacological Study of the Compounds of the Invention

EXAMPLE 37: STUDY OF THE ACUTE TOXICITY

The acute toxicity was assessed after the oral administration of a dose of 1000 mg.kg$^{-1}$ to batches of 8 mice (26±2 grams). The animals were observed at regular intervals during the first day, and daily during the 2 weeks following the treatment.

It is apparent that the compounds of the invention are completely non-toxic. No deaths are observed after administration of a dose of 1000 mg.kg$^{-1}$. No disorders are noted after administration of this dose.

EXAMPLE 38: STUDY OF THE ANALGESIC ACTIVITY

The activity against pain was investigated in mice (23–25 g) according to a protocol derived from the technique described by SIEGMUND (SIEGMUND E.A., R.A. CADMUS & GOLU, J. Pharm. Exp. Ther. 119, 1874, 1954). The mice, randomized in batches of 12 animals, received the treatment orally (excipient for the controls) 1 hour before the intraperitoneal injection of a 0.02% strength aqueous-alcoholic solution of phenyl-p-benzoquinone (Sigma). The writhing movements are counted between the 5th and 10th minute after injection.

The percentage activity obtained was evaluated for each dose (% decrease in the number of writhing movements in the treated animals relative to the controls). An $ED_{50}$, the dose producing a 50% activity, was determined for each product.

It was apparent that some compounds of the invention possess a very advantageous analgesic activity. Thus, the $ED_{50}$ of the compound of Example 6 is in the region of 5 mg.kg$^{-1}$.

By way of comparison, the administration of a dose of 100 mg.kg$^{-1}$ of the compounds of French Patent 73/23,280 produced a percentage analgesic effect—in a comparable test—of the order of 25 to 60%, and the compound of French Patent 80/20,861, the analgesic activity of which is the most advantageous, had an $ED_{50}$ of 9 mg.kg$^{-1}$ in this same Siegmund test, that is to say almost twice as large as that of the most advantageous product of the present invention.

EXAMPLE 39: STUDY OF THE ANTI-INFLAMMATORY ACTIVITY

The anti-inflammatory potential of the compounds was investigated on a model of acute inflammation induced by the subcutaneous injection of a solution of carrageenan into the rat hind foot, according to a technique based on the method of WINTER, C.A., E.A. RISLEY and G.N. NUSS (Proc. Soc. Exp. Med. 111, 554, 1962). The rats (100–120 g), randomized in batches of 8, were treated (including the controls, which receive excipient) 1 hour before the local injection of a 0.5% strength suspension of carrageenan (Sigma type IV; 0.1 ml per rat). The edema is determined 3 hours after injection, by plethysmometric measurement (UGO BASILE water plethysmometer) of the volume of each of the hind feet (edema = volume of the inflamed foot less the volume of the non-inflamed foot).

It is apparent that the products of the invention have no activity in this test. In comparison, the products of French Patent 73/23,280 possess an anti-inflammatory activity.

EXAMPLE 40: RESERPINE ANTAGONISM

The reserpine antagonism was assessed after the administration of reserpine (2.5 mg.kg$^{-1}$) to a batch of 6 mice. Four hours later, the test compound is administered intraperitoneally. A control batch receives no product.

Two parameters are observed rectal temperature and ptosis. In the controls, reserpine administration leads to closing of the eye and a substantial fall in rectal temperature.

The administration of some compounds of the invention antagonizes the effects of reserpine, which demonstrates the antidepressant activity of these de compounds.

EXAMPLE 41: ANTIHYPERTENSIVE ACTIVITY

The arterial blood pressure was determined on the rat's tail according to the method described by BYROM and WILSON (1938). This method consists in measuring the pressure required to interrupt the blood flow in the caudal artery. To this end, a pneumatic rubber cuff linked to a NARCO type PE 300 electrosphygmomanometer is attached to the rat's tail 2 centimeters from the base, so as to compress the caudal artery.

A pneumatic type pulsation sensor permits auscultation of the artery 1 cm downstream from the cuff. The value of the systolic blood pressure is that at which reappearance of the systolic/diastolic fluctuations is observed during deflation of the cuff.

The products of the invention are administered orally in suspension in acacia syrup in a volume of 1 ml.kg$^{-1}$.

The pressure is measured before any treatment is given, and 2 hours and 24 hours after the treatment.

Some products of the invention significantly lower the arterial blood pressure.

EXAMPLE 41: PHARMACEUTICAL COMPOSITION TABLET

Tablets containing 20 mg of 3-methyl-6-(3-morpholinopropyl)benzoxazolinone

| Preparation formula for 1000 tablets. | |
|---|---|
| 3-Methyl-6-(3-morpholinopropyl)-benzoxazolinone | 20 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

What is claimed is:

1. A compound selected from those formula (I):

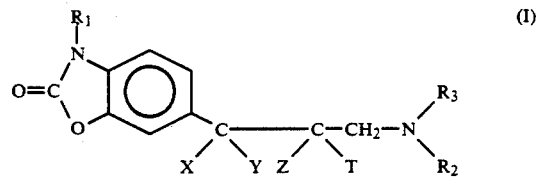

in which:
R$_1$ denotes a hydrogen atom or a lower alkyl group optionally substituted with a hydroxyl group,
R$_2$ and R$_3$ form, with the nitrogen atom to which they are attached a morpholino group,
X denotes a hydrogen atom,
Y denotes a hydroxyl group,
Z denotes a hydrogen atom, and
T denotes a hydrogen atom or lower alkyl group,
the term lower indicating that the groups so described have 1 to 6 carbon atoms inclusive,
their stereoisomers, their quaternary ammonium salts and their addition salts with a pharmaceutically, acceptable acid.

2. A compound as claimed in claim 1 which is 3-methyl-6-(1-hydroxy-3-morpholinopropyl)benzoxazolinone, or an addition salt thereof with a pharmaceutically, acceptable acid.

3. A pharmaceutical composition suitable for alleviation of pain containing, as active analgestic principle, at least one compound as claimed in claim 1, in combination with one or more pharmaceutically, acceptable, nontoxic, inert vehicles or excipients.

4. A pharmaceutical composition as claimed in claim 3, wherein the compound is 3-methyl-6-(1-hydroxy-3- morpholinopropyl)benzoxazolinone or an addition salt thereof with a pharmaceutically-acceptable acid, 5. A method for treating a living animal body afflicted with pain, comprising the step of administering to the said living animal an effective analgesic amount of a compound selected from those of formula (I):

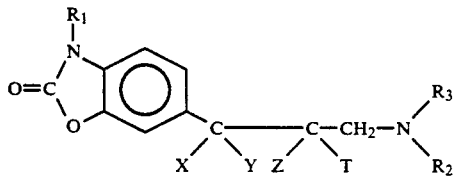

in which:

$R_1$ denotes a hydrogen atom or a lower alkyl group optionally substituted with a hydroxyl group, $R_2$ and $R_3$ form, with the nitrogen atom to which they are attached a morpholino group, X denotes a hydrogen atom, Y denotes a hydroxyl group, Z denotes a hydrogen atom, and T denotes a hydrogen atom or lower alkyl group, the term "lower" indicating that the groups so described have 1 to 6 carbon atoms, inclusive, their stereoisomers, their quaternary ammonium salts, and their addition salts with a pharmaceutically-acceptable acid, which is suitable for the alleviation of said condition.

6. A method as claimed in claim 5, wherein the compound is 3-methyl-6-(1-hydroxy-3-morpholinopropyl)-benzoxazolinone or an addition salt thereof with a pharmaceutically-acceptable acid.

* * * * *

UNITED STATES PATENT AND TRADEMARK OFFICE
CERTIFICATE OF CORRECTION

PATENT NO. : 5,182,278

DATED : Jan. 26, 1993

INVENTOR(S) : Daniel Lesieur, Charles Lespagnol, Jacqueline Bonnet

It is certified that error appears in the above-identified patent and that said Letters Patent is hereby corrected as shown below:

Title Page, [56] References Cited, FOREIGN PATENT DOCUMENTS, third line; "82-11186 should read -- 82-01186 --.

Title Page, [57] ABSTRACT, line 10; move the closing parenthesis ")" from the beginning of the 10th line to the end of the 9th line and insert before the hyphen.

Column 2, line 24; insert -- Y -- before "denotes".

Column 2, line 26; "R" should read -- $R_1$ --.

Column 4, approximately line 26; "$R_3$ T" should read -- $R_3$ and T --.

Column 4, approximately line 44, 45; "compound formula" should read -- compound of formula --.

Column 9, approximately lines 32/33; "for hour" should read -- for 1 hour --.

Column 10, line 16; "condenser 0.04" should read --condenser. 0.04 --.

Column 10, line 63; "condenser 0.045" should read -- condenser. 0.02.

Column 11, approximately line 15; "stirrer 0.02" should read -- stirrer. 0.045 --.

Column 12, lines 27/28; "adding (0.072 mole" should read -- adding 7 $cm^3$ (0.072 mole) --.

Column 14, line 49; "-lpiperazinly)" should read --1-piperazinyl)--.

Column 17, line 54; "observed rectal" should read -- observed: rectal --.

Column 18, approximately line 18; "COMPOSITION TABLET" should read -- COMPOSITION : TABLET --.

Column 18, line 33; "those formula" should read --those of formula --.

Column 18, approximately line 48; "attached a" should read -- attached, a --.

Column 18, approximately line 53; "lower" should read --"lower"--.

Column 18, lines 56/57; "pharmaceutically,acceptable" should read -- pharmaceutically-acceptable--.

UNITED STATES PATENT AND TRADEMARK OFFICE
CERTIFICATE OF CORRECTION

PATENT NO. : 5,182,278
DATED : Jan. 26, 1993
INVENTOR(S) : Daniel Lesieur, Charles Lespagnol, Jacqueline Bonnet It is certified that error appears in the above-identified patent and that said Letters Patent is hereby corrected as shown below:

Column 18, lines 60/61; "pharmaceutically, acceptable acid." should read -- pharmaceutically-acceptable acid. --.

Column 18, line 65; "pharmaceutically, acceptable," should read -- pharmaceutically-acceptable, --.

Column 18, line 66; delete "inert".

Signed and Sealed this

Twenty-second Day of February, 1994

*Attest:*

BRUCE LEHMAN

*Attesting Officer*   *Commissioner of Patents and Trademarks*